United States Patent [19]

Haikala et al.

[11] Patent Number: 5,905,078
[45] Date of Patent: May 18, 1999

[54] USE OF A PYRIDAZINONE DERIVATIVE

[75] Inventors: Heimo Haikala, Espoo; Piero Pollesello, Grankulla; Juha Kaivola, Helsinki; Jouko Levijoki, Espoo, all of Finland

[73] Assignee: Orion Corporation, Finland

[21] Appl. No.: 09/099,945

[22] Filed: Jun. 19, 1998

[51] Int. Cl.⁶ .................................................. A61K 31/495
[52] U.S. Cl. ................................................................ 514/247
[58] Field of Search ............................................... 514/247

[56] References Cited

U.S. PATENT DOCUMENTS 3,746,712  7/1973  Ross et al. .
4,397,854  8/1983  Sircar .

FOREIGN PATENT DOCUMENTS 3163050  7/1991  Japan .
4368328  12/1992  Japan .

OTHER PUBLICATIONS

Robertson, D. W. et al., "Dihydropyridazinone Cardiotonics: The Discovery and Inotropic Activity of 1, 3–Dihydro–3, 3–dimethyl–5–(1,4,5, 6–tetrahydro–6–oxo–3–pyridazinyl)–2H–indol–2–one", J. Med. Chem. 29, 1986, 1832–1840.

Teikoku Hormone Mfg Ltd, "Novel optically active butyric acid deriv.—obtd. by catalytically hydrogenating butenoic acid derivs., in presence of ruthenium (II) complex(es) for use in pharmaceuticals", Derwent WPI abstract of Japanese Patent Application JP 3163050 published Jul. 15, 1991, Derwent Info Ltd., Week 9134.

Yasuda, K. et al., "Preparation of optically active aminobenzoylbutyric acid derivatives as intermediates for .beta.–blockers and antihypertensives", Chemical Abstracts abstract of Japanese Patent Application JP 3163050 published Jul. 15, 1991, CA 116:106784.

Teikoku Hormone Mgf Co Ltd, "Agent for treating chronic renal failure—contains 6–(4–acetyl–aminophenyl)–4, 5–dihydro–5–methyl–3(2H)–pyridazinone", Derwent WPI abstract of Japanese Patent Application JP 4368328 published Dec. 21, 1992, Derwent Info Ltd., Week 9314.

Myasaka, K. et al., "A pyridazinone for treatment of chronic heart failure", Chemical Abstracts abstract of Japanese Patent Application JP 4368328 published Dec. 21, 1992, CA 118:198216.

Ishimori, T. et al., "Cardiac Effects of the Novel Pyridazinone Derivative 6–|4–|2–|3–(5–Chloro–2–cyanophenoxy)–2–hydroxypropylamino| –2–methylpropylamino|–4,5–dihydro–5–methyl–3(2H) pyridazinone Monoethyl Maleate and Its Metabolite in Isolated Heart Preparations of Guinea Pigs and Dogs", Arzneim.–Forch. /Drug Res. 44(1), Nr. 5, 1994, 583–588.

Primary Examiner—Raymond Henley, III
Attorney, Agent, or Firm—Finnegan, Henderson, Farabow, Garrett & Dunner, L.L.P.

[57] ABSTRACT

A method for the treatment of neurohumoral imbalance caused by alterations of cardiac function to prevent the development of heart failure comprises administering an effective amount of (R)-|4-(1,4,5,6-tetrahydro-6-oxo-3-pyridazinyl)phenyl|acetamide to a mammal in need of such treatment.

6 Claims, No Drawings

USE OF A PYRIDAZINONE DERIVATIVE

The intention relates to a method for the treatment of neurohumoral imbalance caused by alterations of cardiac function to prevent the development of heart failure by administering an effective amount of (R)-N-|4-(1,4,5,6-tetrahydro-6-oxo-3-pyridazinyl)phenyl|acetamide to a mammal in need of such treatment.

Racemic N-|4-(1,4,5,6-tetrahydro-6-oxo-3-pyridazinyl) phenyl|acetamide (I) has been described earlier as a hypotensive agent (U.S. Pat. No. 3,746,712) and as a cardiotonic agent having inotropic activity (U.S. Pat. No. 4,397,854). It has been reported that the inotropic action of racemic N-|4-(1,4,5,6-tetrahydro-6-oxo-3-pyridazinyl)phenyl|acetamide is based on phosphodiesterase III (PDE III) enzyme inhibition (Ishimori t. et al., Arzneim.- Forsch. (1994), 44(5), 583–8). The compound (I) has an asymmetric carbon atom and may therefore exist in two stereoisomeric forms. The (R)- and (S)- enantiomers of (I) has been earlier described in Japanese patent application no. (Heisei) JP 3163050. However, biological activity data for the enantiomers has not been described.

At the moment series of inotropic compounds, e.g. milrinone, the mechanism of which is based on PDE III inhibition are in clinical trials for the treatment of heart failure. These compounds increase the contractility of the cardiac muscle by increasing the calcium current into the cardiac muscle and produce vasodilatation. The contraction in cardiac muscle is triggered by the binding of calcium in troponin. However, it is possible that the long-term application of PDE III inhibitors leads to calcium overload in the cardiac muscle which can trigger arrhythmias. Therefore, the main mechanism to increase cardiac contractility should be a mechanism which does not produce calcium overload. The enhancement of the turnover of intracellular calcium released from sarcoplasmic reticulum and the increase of calcium sensitivity of contractile proteins are such mechanisms which do not induce calcium overload.

When a patient has harmful alterations in the cardiac function, the contractility of the cardiac muscle can still be maintained through neurohumoral activation in the body, which increases the intake of calcium in the cardiac muscle. In this situation the calcium overload can trigger arrhythmias, and prolonged neurohumoral activation will accelerate the development of heart failure. Neurohumoral imbalance can be indicated, for example, by altered renin and noradrenaline concentrations in a patient's plasma. PDE III inhibitors can not be used chronically in the treatment of neurohumoral imbalance because they further increase the intake of calcium into the cardiac muscle. However, the use of a calcium sensitizer can sufficiently increase the contractility already in normal and decreased calcium concentrations which would reduce the need of neurohumoral activation and thereby prevent the development of heart failure.

It has been now discovered that the (R)-enantiomer of N-|4-(1,4,5,6-tetrahydro-6-oxo-3-pyridazinyl)phenyl| acetamide has a calcium sensitizing effect on troponin and that its main mechanism to increase cardiac contractility is the increase of calcium sensitivity of troponin. This was unexpected since the mechanism of rasemic compound (I) was reported to be PDE III inhibition. Thus, being a calcium sensitizer the (R)-enantiomer of N-|4-(1,4,5,6-tetrahydro-6-oxo-3-pyridazinyl)phenyl|acetamide has a utility in the treatment of neurohumoral imbalance caused by alterations of cardiac function to prevent the development of heart failure.

The present invention relates to a method for the treatment of neurohumoral imbalance caused by alterations of cardiac function to prevent the development of heart failure by administering orally or parenterally in a solid or liquid dosage form an effective amount of (R)-enantiomer of compound (I) to a patient in need of such treatment.

The pharmaceutically active compound according to this invention is formulated into dosage forms using the principles known in the art. It is given to a patient as such or in combination with suitable pharmaceutical excipients in the form of tablets, dragees, capsules, suppositories, emulsions, suspensions or solutions. The composition according to the invention contains a therapeutically effective amount of the pharmaceutically active compound of the invention. The contents of the active compound is in the composition from about 0.5 to 100% per weight.

In the claimed method the compound of the invention may be administered to man in oral doses ranging from about 0.1 to 500 mg, preferably 0.5 to 10 mg, per day. Choosing suitable ingredients for the composition is a routine for those of ordinary skill in the art. It is evident that suitable carriers, solvents, gel forming ingredients, dispersion forming ingredients, antioxidants, colours, sweeteners, wetting compounds and other ingredients normally used in this field of technology may be also used.

The following example will further illustrate the invention.

EXAMPLE 1

Preparation of (R)-N-|4-(1,4,5,6-tetrahydro-4-methyl-6-oxo-3-pyridazinyl)phenyl|acetamide (R)-6-(4-aminophenyl)-4,5-dihydro-5-methyl-3(2H)-pyridazinone (30.0 g) and acetonitrile (600 mL) were mixed and the mixture was refluxed until the starting material dissolves. Acetic anhydride (30.0 mL) was added to the refluxing mixture. After 10 min the solution was allowed to cool to room temperature. The product was filtered, washed with acetonitrile and dried.

Yield 30.8 g, mp 230–232, $^1$H-NMR (DMSO-d$_6$, 400 MHz) 1.06 (d, 3H, J=7.3 Hz), 2.06 (s, 3H), 2.22 (d, 1H, J=16.6 Hz), 2.67 (dd, 1H, J=16.6 Hz, 6.8 Hz), 3.35 (m, 1H), 7.63 (d, 2H, J=8.8 Hz), 7.72 (d, 2H, J=8.8 Hz), 10.09 (s, 1H), 10.88 (s, 1H). $[\alpha]_D^{20}$=–466° (c=2 mg/ml, DMF).

The usefulness of the compound of the invention is demonstrated by the following experiments. Compound A is (R)-N-|4-(1,4,5,6-tetrahydro-6-oxo-3-pyridazinyl)phenyl| acetamide.

Calcium Sensitizing Effect in Skinned Cardiac Fiber

Left ventricular papillary muscle of the guinea-pig was dissected and rinsed in ice-cold Tyrode solution. Thereafter the papillary muscle was immersed into a solution containing (mM): Potassium acetate 74.7, EGTA 10, MgSO$_4$ 5.4, ATP-Na$_2$ 4, DTE 1, MOPS 20, pH 7.0 (by 1 M KOH). Subsequently, the papillary muscle was sonicated at 10 Watt for 60 sec in this ice-cold solution. The distance between ultrasound probe and the papillary muscle was 10 mm. The fibers (<200 µm in diameter) were dissected from surface of sonicated papillary muscles. Moreover, the sonicated and dissected fibers were kept for 30 min in a "skinning" solution (ice-cold) containing saponin (250 µg/ml) in addition to the other constituents. Continuous magnetic stirring was used during this treatment.

The fibers which were further dissected (<100 µm in diameter) were then mounted horizontally with a glue (cellulose acetate in acetone) between a steel-rod extension of isometric force transducer (AME-801 strain gauge, Horten Electronics, Norway) and a glass rod attached to a micro-manipulator. The force transducer was connected to an amplifier. The fibers were kept in the "relaxing" solution containing (mM): imidazole 30, ATP-Na$_2$ 10, NaN$_3$ 5, EGTA 5, MgCl$_2$ 12.5, and 350 U creatinkinase. The temperature of the solution was 22° C. and the pH was set to 6.7 by 1 M KOH. The ionic strength was adjusted with 1 M KCl to correspond that of the "activating" solution. The composition of the "activating" solution was the same as that of the "relaxing" solution except that it contained also CaCl$_2$. The fibers were induced to contract in desired free pCas (-log [Ca$^{2+}$]) which were obtained by properly mixing of the "relaxing" and "activating" solutions. Tension produced by a fiber at pCa 4.8 was taken as maximum response. At the beginning of the experiment the fiber was stretched as described above.

TABLE 1

Calcium sensitizing effect in skinned fiber at pCa 5.6

|  |  | Change in force/ % of control |
|---|---|---|
| Compound A | 0.3 µM | + 26 ± 6 (n = 7) |
|  | 3 µM | + 109 ± 35 (n = 7) |
| Milrinone |  | ineffective |

Positive Inotropic Effect in Paced Cardiac Muscle

Four weeks old guinea-pigs weighing about 350 g were used. In the experiments the right ventricular papillary muscle of the heart was mounted for measurement of isometric tension in organ bath containing modified Tyrode solution (37° C.) bubbled with 95% O$_2$, 5% CO$_2$. The composition of the modified Tyrode solution was (mM): NaCl 135; MgCl$_2$.6H$_2$O 1; KCl 5; CaCl2.2H$_2$O 2; NaHCO$_3$ 15; Na$_2$HPO$_4$.2H$_2$O 1; glucose 10; pH 7.3–7.4. The volume of the open horizontal chamber was 1 ml and flow rate of the superfusion solution running through the chamber was 5 ml/min. Papillary muscle (<1 mm in diameter) was stretched horizontally between force-displacement transducer (FT 0.3 C) and a needle fixed to the bottom of the chamber. An initial stretching tension of 300 mg was applied to the muscle which was electrically stimulated (Stimulator model SEC 48 F, Grass Instruments) via platinum field electrodes at 1 Hz with rectangular pulses (duration 4 ms). The stimulation occurred at twice threshold voltage in order to achieve simultaneous activation of all myocytes in the capillary muscle. A force-displacement transducer was connected to a polygraph D.C. driver amplifier (model 7 DA, Grass Instruments) and a programmable scanner (model SI 5010, Tetronix). The amplified signal was digitised with 1 kHz frequency by a programmable digitizer (model 390 A, Sony Tetronix).

TABLE 2

Positive inotropic effect in guinea-pig papillary muscle

|  | EC$_{50}$/µM |
|---|---|
| Compound A | 0.1 |
| Milrinone | 2 |

We claim:

1. A method for the treatment of neurohumoral imbalance caused by alterations of cardiac function to prevent the development of heart failure by administering an effective amount of (R)-[4-(1,4,5,6-tetrahydro-6-oxo-3-pyridazinyl)phenyl]acetamide to a mammal in need of such treatment.

2. The method according to claim 1, wherein said compound is administered to a human in oral doses ranging from 0.1 to 500 mg per day.

3. The method according to claim 2, wherein said compound is administered in oral doses ranging from 0.5 to 10 mg per day.

4. A method of increasing calcium sensitivity of troponin, which method comprises administering an effective amount of (R)-[4-(1,4,5,6-tetrahydro-6-oxo-3-pyridazinyl)phenyl] acetamide to a mammal.

5. The method according to claim 4, wherein said compound is administered to a human in oral doses ranging from 0.1 to 500 mg per day.

6. The method according to claim 5, wherein said compound is administered in oral doses ranging from 0.5 to 10 mg per day.

* * * * *

UNITED STATES PATENT AND TRADEMARK OFFICE
CERTIFICATE OF CORRECTION

PATENT NO.    : 5,905,078                                         Page 1 of 1
DATED         : May 18, 1999
INVENTOR(S)   : Heimo Haikala et al.

It is certified that error appears in the above-identified patent and that said Letters Patent is hereby corrected as shown below:

In the Abstract,
Change "(R)-[4-(1,4,5,6-tetrahydro-6-oxo-3-pyridazinyl)phenyl]acetamide" to
-- (R)-N-[4-(1,4,5,6-tetrahydro-4-methyl-6-oxo-3-pyridazinyl)phenyl]acetamide --.

Column 1,
Lines 6-7, change "(R)-N-[4-(1,4,5,6-tetrahydro-6-oxo-3-pyridazinyl)phenyl]acetamide"
to -- (R)-N-[4-(1,4,5,6-tetrahydro-4-methyl-6-oxo-3-pyridazinyl)phenyl] acetamide --;
Lines 9-10, change "N-[4-(1,4,5,6-tetrahydro-6-oxo-3-pyridazinyl)phenyl]acetamide"
to -- N-[4-(1,4,5,6-tetrahydro-4-methyl-6-oxo-3-pyridazinyl)phenyl]acetamide --;
Lines 14-15, change "N-[4-(1,4,5,6-tetrahydro-6-oxo-3-pyridazinyl)phenyl]acetamide"
to -- N-[4-(1,4,5,6-tetrahydro-4-methyl-6-oxo-3-pyridazinyl)phenyl]acetamide --;
Lines 54-55, change "N-[4-(1,4,5,6-tetrahydro-6-oxo-3-pyridazinyl)phenyl]acetamide"
to -- N-[4-(1,4,5,6-tetrahydro-4-methyl-6-oxo-3-pyridazinyl)phenyl]acetamide --;
Lines 61-62, change "N-[4-(1,4,5,6-tetrahydro-6-oxo-3-pyridazinyl)phenyl]acetamide"
to -- N-[4-(1,4,5,6-tetrahydro-4-methyl-6-oxo-3-pyridazinyl)phenyl]acetamide --.

Column 2,
Lines 28-29, change "(R)-N-[4-(1,4,5,6-tetrahydro-6-oxo-3-pyridazinyl)phenyl]
acetamide" to -- (R)-N-[4-(1,4,5,6-tetrahydro-4-methyl-6-oxo-3-pyridazinyl)phenyl]
acetamide --.

Column 4,
Lines 25-26, change "(R)-[4-(1,4,5,6-tetrahydro-6-oxo-3-pyridazinyl)phenyl]acetamide"
to -- (R)-N-[4-(1,4,5,6-tetrahydro-4-methyl-6-oxo-3-pyridazinyl)phenyl]acetamide --.
Lines 35-36, change "(R)-[4-(1,4,5,6-tetrahydro-6-oxo-3-pyridazinyl)phenyl]acetamide"
to --(R)-N-[4-(1,4,5,6-tetrahydro-4-methyl-6-oxo-3pyridazinyl)phenyl]acetamide --.

Signed and Sealed this

Fourth Day of September, 2001

*Nicholas P. Godici*

Attest:

Attesting Officer

NICHOLAS P. GODICI
*Acting Director of the United States Patent and Trademark Office*